United States Patent
Heitzmann

[11] Patent Number: 5,957,912
[45] Date of Patent: Sep. 28, 1999

[54] CATHETER HAVING DISTAL STYLET OPENING AND CONNECTOR

[75] Inventor: Harold A. Heitzmann, Irvine, Calif.

[73] Assignee: Camino Neurocare, Inc., San Diego, Calif.

[21] Appl. No.: 09/061,761

[22] Filed: Apr. 16, 1998

[51] Int. Cl.⁶ ................................................ A61M 25/16
[52] U.S. Cl. ...................... 604/533; 604/523; 604/284; 604/905; 600/561
[58] Field of Search .................................. 604/35, 65, 66, 604/67, 93, 164, 170, 264, 280, 282, 283, 284, 902, 905; 600/480, 486, 488, 561

[56] References Cited

U.S. PATENT DOCUMENTS

| | | |
|---|---|---|
| 4,111,603 | 9/1978 | Wilkinson . |
| 4,661,110 | 4/1987 | Fortier et al. .......................... 604/256 |
| 4,903,707 | 2/1990 | Knute . |
| 5,065,010 | 11/1991 | Knute . |
| 5,107,847 | 4/1992 | Knute et al. . |
| 5,108,364 | 4/1992 | Takezawa et al. . |
| 5,191,898 | 3/1993 | Millar . |
| 5,201,730 | 4/1993 | Easley et al. ............................. 606/4 |
| 5,312,357 | 5/1994 | Buijs et al. ............................. 604/164 |
| 5,405,339 | 4/1995 | Kohnen et al. ......................... 604/283 |
| 5,423,768 | 6/1995 | Folden et al. ........................... 604/200 |
| 5,437,284 | 8/1995 | Trimble . |
| 5,531,679 | 7/1996 | Schulman et al. ....................... 604/65 |
| 5,579,774 | 12/1996 | Miller et al. . |
| 5,830,196 | 11/1998 | Hicks ..................................... 604/280 |
| 5,846,219 | 12/1998 | Vancaillie ............................... 604/35 |
| 5,891,101 | 4/1999 | Wilcox et al. .......................... 604/175 |

FOREIGN PATENT DOCUMENTS 0 447 545 B1  3/1994  European Pat. Off. ......... A61M 1/00

*Primary Examiner*—Corrine McDermott
*Assistant Examiner*—LoAn H. Thanh
*Attorney, Agent, or Firm*—Fulwider Patton Lee & Utecht, LLP

[57] ABSTRACT

An intracranial pressure monitoring and drainage catheter having two tubes that are joined into a single tube at the catheter body distal end, each tube having a separate lumen. One tube is severed at a location proximal to the catheter body distal end and has an internal connector that may be removed from one severed end to introduce a stylet into the lumen. The stylet results in increased rigidity of the catheter body distal end to assist in placing the catheter in the patient. The wall of the distal end of the catheter has drainage apertures formed in communication with the lumen in which the stylet is placed. Reconnecting the internal connector after removal of the stylet provides a fluid path from the distal end of the catheter body to the proximal end of the catheter for drainage of fluid from the patient. A sensor may be placed in the other lumen for sensing a physical parameter of the patient, such as pressure or temperature or both.

27 Claims, 4 Drawing Sheets

CATHETER HAVING DISTAL STYLET OPENING AND CONNECTOR

The invention pertains generally to catheters, and more particularly, to a catheter that is more easily insertable into a mammalian skull with a stylet to facilitate the drainage of intracranial fluid.

BACKGROUND

Head injuries and various diseases have been known to cause increases in intracranial pressure, which can pose a danger to the patient. Large uncontrolled increases in intracranial pressure may result in brain injury or impairment, permanent or temporary, of neuromotor functions. Thus, in some patients, it is desirable to monitor the intracranial pressure, and to provide a means for draining excess cerebrospinal fluid from the cranial vault to control the pressure when such drainage is indicated.

Because pressure monitoring and drainage procedures are invasive, some degree of trauma to the patient occurs. It is desirable to keep such trauma to a minimum while still allowing the invasive instrument to perform its function. In the case of drainage, a relatively large lumen or set of lumina are desired so that the fluid can be drained at a relatively fast rate and the pressure can be brought rapidly under control. However, the size of the catheter containing such lumina must be limited so that trauma to the patient is not excessive. In many cases, it is preferable to also insert a pressure sensor into the cranial cavity to directly measure intracranial pressure for increased accuracy. Pressure sensors typically involve multiple parts and may likewise be of substantial size, although it is desirable to limit their size also to reduce trauma to the patient.

Typically, intracranial pressure monitoring catheters and ventricular drainage catheters have been insertable into the patient through a burr hole formed in the skull. In some instances, the catheters have been designed for insertion through a subcutaneous tunnel which extends beneath the patient's scalp, adjacent the skull burr hole through which the catheter is inserted. It is believed that such scalp tunnel insertion techniques decrease the risk of intracranial infection. Providing an elongate tunnel through which pathogenic organisms would have to pass prior to passing through the skull burr hole and into the cranium makes it much more difficult for such organisms to enter the cranium.

During the treatment of a patient where control of the cranial pressure is necessary through drainage of the cerebrospinal fluid, it is desirable to monitor the pressure while the fluid is being drained so that excessive drainage does not occur. However, placing two separate catheters in the cranium, one containing a pressure sensor and the other containing a drainage lumen, is undesirable due to the trauma to the patient that would result and the increased chances for infection. In some cases, treatment for severe head injuries or diseases can take many days if not longer and exposing the cranium to the possibility of infection through the insertion of two separate catheters may be clinically unacceptable.

Another consideration in the construction of a ventricular catheter is the method of insertion of the catheter distal end into the proper location in the cranium. In some cases, a lumen exists in the catheter for receipt of a stylet. The entry burr hole is made in the skull of the patient, the insertion stylet is inserted into the closed lumen of the distal end of the catheter, and is used to force the catheter through the entry burr hole of the patient and into position. The stylet is then withdrawn and pressure monitoring and drainage procedures begun as necessary. In such a catheter, the stylet must be stiff enough to force the catheter into operational position in the cranium and therefore must have a certain minimum thickness. Additionally, the stylet-receiving lumen in the catheter body must be large enough to accept the stylet, yet strong enough so that the stylet will not puncture the catheter distal tip when introducing the catheter into the patient's skull with the stylet. Because the pressure sensor also has a finite size, and the outer size of the catheter is limited, typically the drainage lumen is smaller than is desirable. This can adversely affect the drainage rate.

In some prior art devices, a ventricular drainage catheter would typically be inserted into the patient. If pressure monitoring were needed, a pressure monitoring catheter would be inserted through the drainage lumen in the drainage catheter, thereby lowering the drainage capability of the drainage catheter.

An example of a catheter that overcomes some of the above deficiencies is shown in U.S. Pat. No. 5,312,357 to Buijs et al. This catheter includes a lumen that may receive a pressure sensor device and another lumen for receiving a stylet for insertion of the catheter into the patient and for drainage once the stylet is removed. However, the closure device is shown as a sleeve that is slid over the opening for the stylet. Such a closure technique can be difficult to use due to the need to slide it over a substantial length of tubing.

It is important that the sleeve make a fluid-tight seal over the stylet opening so that drainage is directed to the proximal end of the catheter. A tight-fitting seal, however, will tend to be difficult to slide into place. Also, a less difficult to slide seal may not fit tightly enough to prevent leakage.

Hence those skilled in the art have recognized a need for a combination pressure monitoring and drainage catheter that has a small outer diameter for reduced trauma to the patient while having the ability to monitor pressure, allow drainage of the fluid in the cranium, and accept a stylet for use in placement of the catheter in the correct position in the cranium. In addition, it has also been recognized that using one large lumen for both drainage and receiving the stylet for installation is desirable. Further, those skilled in the art have recognized a need for an easier means to close the opening of a lumen used to receive a stylet. The present invention fulfills these needs and others.

SUMMARY OF THE INVENTION

Briefly and in general terms, the present invention is directed to a catheter comprising first and second elongate tubes, each tube having a lumen and each tube having distal and proximal ends, wherein the first and second tubes are joined together at their distal ends to form a single tube defining a catheter body distal end, with the lumina of the first and second tubes remaining separate in the catheter body distal end, the first tube having first and second segments with the first segment being located distally to the second segment, the lumen of the first segment terminating in a closed end in the catheter body distal end, and the first and second segments being severed from each other at a location proximal to the catheter body distal end, and a connector engaged with the first and second segments and connecting the first and second segments together at the severance location, the connector forming a fluid-tight seal with the first and second segments, wherein the length of the lumen of the first segment continuing into the catheter body distal end and the diameter of the lumen are selected to receive a stylet so that the stylet can be introduced through the first segment lumen and extended to the closed end of the segment.

In a further aspect, the connector comprises an internal connector disposed in the lumina of both the first and second segments, the connector having a fluid lumen that is in fluid communication and interconnects the lumina of the first and second segments. The connector may be fixed in position in the distal end of the second segment but may be disconnected from the proximal end of the first segment so that a stylet may be inserted into the proximal end of the first segment, and then the connector may be reconnected for fluid flow through the lumina of the segments.

In another aspect, the connector may comprise a slidable sleeve disposed on one of the first and second segments and slidable over the other segment for forming a fluid-tight seal between the first and second segments.

In a more detailed aspect, the catheter may comprise a sensor located in the catheter body distal end in one of the lumina of the first and second tubes, the sensor located so as to sense a selected parameter at the distal end of the catheter body. Energy conducting devices are connected to the sensor and are disposed in one of the lumina of the first and second tubes and extend to the proximal end of the catheter body. These devices may comprise electrical conductors or optical fibers coupled to the sensor and extending to the proximal end of the lumen in which they are disposed. The sensor and energy conducting devices may be located in the catheter body distal end in the lumen of the second tube.

In a more detailed aspect, the sensor comprises a pressure sensor disposed in the catheter body distal end and the energy conducting devices comprise optical fibers extending from the pressure sensor to the proximal end of the lumen.

In yet another aspect, the catheter further comprises drainage apertures formed at the catheter body distal end in fluid communication with one of the lumina of the first and second tubes.

The novel features that are believed to be characteristic of the invention together with further objects and advantages thereof will be more readily understood from the following descriptions considered in connection with the accompanying drawings.

DETAILED DESCRIPTION OF THE PREFERRED EMBODIMENTS

Figure 1:
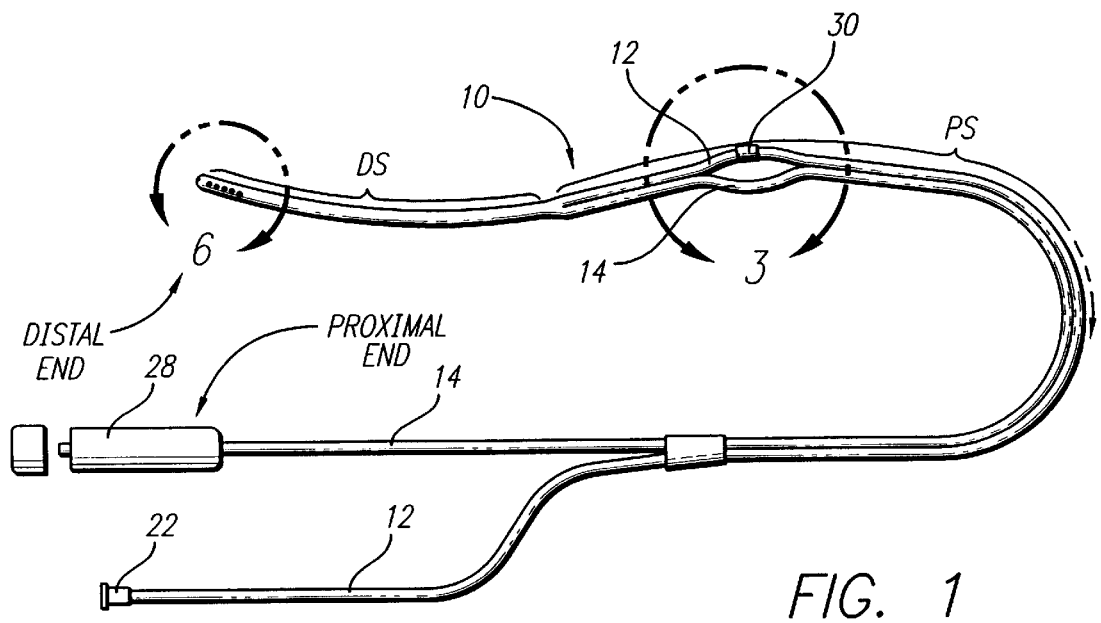
FIG. 1 is a perspective view of an intracranial catheter in accordance with aspects of the present invention.

In the following description, like reference numerals are used to refer to like or corresponding elements in the different figures of the drawings. Referring now to the drawings with more particularity, in FIG. 1 there is shown a catheter 10 that generally comprises an elongate, flexible drainage tube 12 and an elongate flexible pressure monitoring tube 14. Distal portions (i.e., the portions adjacent the distal ends) of the flexible drainage tube 12 and pressure monitoring tube 14 are fused, (i.e., conjoined or commonly contained within a surrounding sheath) so as to form a unitary distal segment DS or the catheter body distal end of the catheter 10. The remaining proximal portions (i.e., those portions proximal to the fused, conjoined or commonly contained distal portion which form the distal segment DS) of the drainage tube 12 and pressure monitoring tube 14 are substantially separate from one another, in side by side relation to one another, and may be joined fully or in part by way of a joining member, such as a tearable plastic strand, web or membrane formed between the adjacent portions of the drainage tube 12 and pressure monitoring tube 14.

Figure 6:
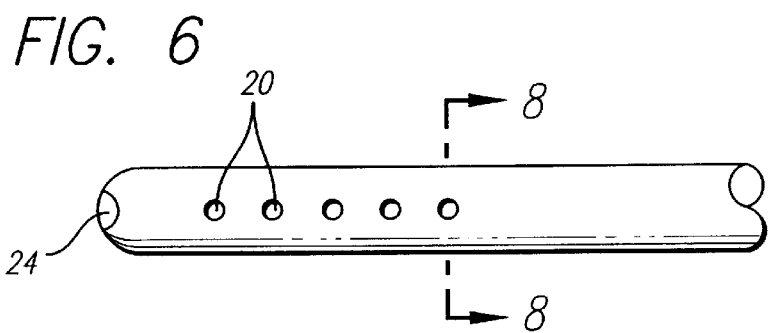
FIG. 6 is an enlarged perspective view of a distal portion of the intracranial catheter of FIG. 1.
Figures 7, 8:
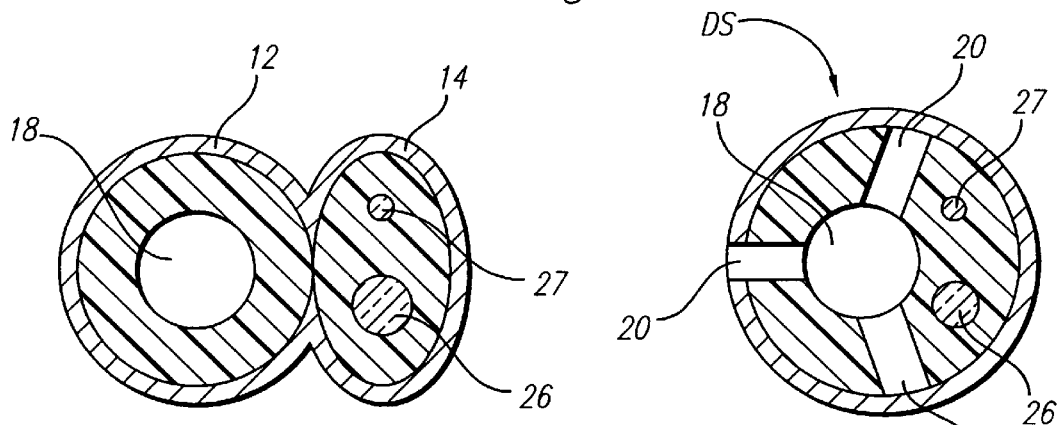
FIG. 7 is a cross sectional view through lines 7—7 of FIG. 5.
FIG. 8 is a cross sectional view through lines 8—8 of FIG. 6.

The drainage tube 12 has a lumen 18 (FIG. 8) that extends longitudinally therethrough. Rows of drainage apertures 20 (FIG. 6) are formed near the distal end of the unitary distal segment DS of the catheter 10. These drainage apertures 20 open into the drainage lumen 18 of the drainage tube 12 (FIG. 8). A Luer connector 22 is affixed to the proximal end of the drainage tube 12, to facilitate coupling of the drainage tube 12 to a separate fluid withdrawal or collection vessel or apparatus. In this regard, cerebrospinal fluid may be drawn in the proximal direction through drainage apertures 20, through lumen 18, and out of the Luer connector 22 on the proximal end of the drainage tube 12.

The pressure monitoring tube 14 houses pressure sensing and transmitting apparatus which is operative to receive or sense the pressure at a location within the cranium, and to transmit such pressure to the proximal end of the pressure monitoring tube 14. The proximal end of the pressure monitoring tube 14 is preferably connectable to an external pressure monitor or other device operative to provide a discernable pressure reading.

Typically, the pressure monitoring tube 14 will be provided with a pressure receiver or sensor 24 (FIG. 6) mounted at a pressure sensing location on the unitary distal segment DS so as to sense pressure at that location. In some instances, the pressure sensor 24 may be located at the distal end of the unitary distal segment DS of the catheter 10. In other embodiments, the pressure sensor 24 may be located on the sidewall of the distal segment DS, at a spaced distance proximal to the distal end of the unitary distal segment DS of the catheter 10. Typically, when the pressure sensor 24 is located on the distal end of the distal segment DS, such pressure sensor 24 will provide a reading of the cerebrospinal fluid pressure within the ventricle of the brain when the distal segment DS of the device is inserted downwardly into the ventricle. Alternatively, in embodiments wherein the pressure sensor 24 is located on the sidewall of the distal segment DS, such pressure sensor 24 will provide a reading of the parenchymal pressure within the brain, at a location between the outer surface of the brain and the brain ventricle to which the distal end of the catheter 10 is inserted.

A pressure transmitting member or pathway 26 (FIG. 7) extends longitudinally through the pressure monitoring tube 14 to transmit pressure changes or indicia of the pressure received or sensed by the pressure sensor 24. Such pressure transmitting member or pathway 26 serves to carry the sensed pressure, or indicia thereof, to the proximal end of the pressure monitor and tube 14. A connector 28 is provided on the proximal end of the pressure monitor and tube 14 to facilitate connection of the pressure transmitting member or pathway 26 to an external monitoring device or other apparatus operative to provide discernable pressure readings in response to changes in pressure, or indicia thereof, received through the pressure transmitting member or pathway 26.

Various types of pressure sensors 24 and transmitting members or pathways 26 may be incorporated into the catheter 10. For example, the pressure sensor 24 may simply comprise an opening or aperture formed at the pressure sensing location on the distal segment DS, and the pressure transmitting pathway or member 26 may comprise a fluid-fillable lumen which extends longitudinally through the pressure monitor and tube 14 to transmit through a fluid (e.g., sterile saline solution) changes in pressure received through the aperture or opening which forms the pressure sensor 24, to the proximal end of the pressure monitoring tube 14. Such fluid filled lumen may terminate proximally in a connector 28 which connects such lumen to an external pressure transducer to provide a reading of intracranial pressure.

Alternatively, the pressure sensor 24 may comprise a small pressure transducer (e.g., an electronic pressure sensor) mounted in or on the distal segment DS of the catheter 10 at a desired location, and the pressure transmitting member or pathway 26 of such embodiment may comprise an elongate wire which extends longitudinally through the pressure monitor and tube 14 to transmit indicia of pressure from the pressure transducer which forms the pressure sensor 24 to the proximal end of the pressure monitor and tube 14. Such wire is then connectable, via proximal connector 28, to an external pressure monitor or other device operative to provide discernable indicia of the pressure being sensed by the transducer.

In yet another embodiment, the pressure sensing member 24 may comprise an optical sensor mounted on or in the distal segment DS of the catheter 10 at a desired pressure sensing location, and the pressure transmitting member or pathway 26 will comprise one or more optical fibers extending longitudinally through the pressure monitor and tube 14. In such optical embodiment, the proximal connector 28 will comprise an optical connector operative to connect the optical fiber(s) which form the pressure transmitting member or pathway 26 to an external pressure monitor or other device operable to receive optical indicia of pressure and to convert such optical indicia of pressure into discernable pressure readings.

Also, in such optical embodiments of the catheter 10, the fragility of the optical fibers which form the pressure transmitting member or pathway 26 will make it desirable to include an optional tensile member 27 (FIGS. 7 and 8), such as a wire, within the body of the pressure monitor and tube 14 and distal segment DS so as to prevent the optical fiber(s) from becoming kinked or stretched in a manner which could result in breakage of the optical fiber(s). Such tensile member 27 is an optional portion of the catheter 10 and typically will not be included in embodiments of the device wherein the pressure sensor 24 and pressure transmitting member or pathway 26 are other than optical (e.g., fluid column electronic). Examples of optical pressure sensors 24, optical pressure transmitting members or pathways 26 optical connectors 28 and tensile members 27 which may be used in conjunction with an optical embodiment of the catheter 10 are described in copending U.S. patent application Ser. No. 08/130,634, the entirety of which is expressly incorporated herein by reference.

Figure 2:
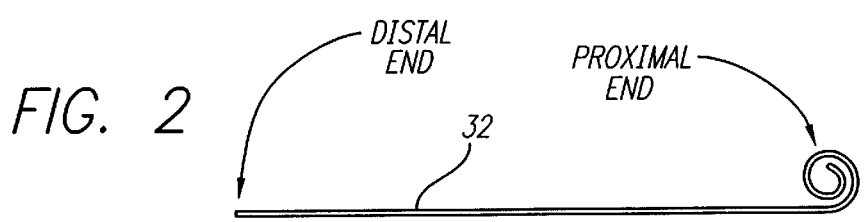
FIG. 2 is a side elevational view of a stylet member useable in conjunction with the intracranial catheter of FIG. 1.
Figure 3:
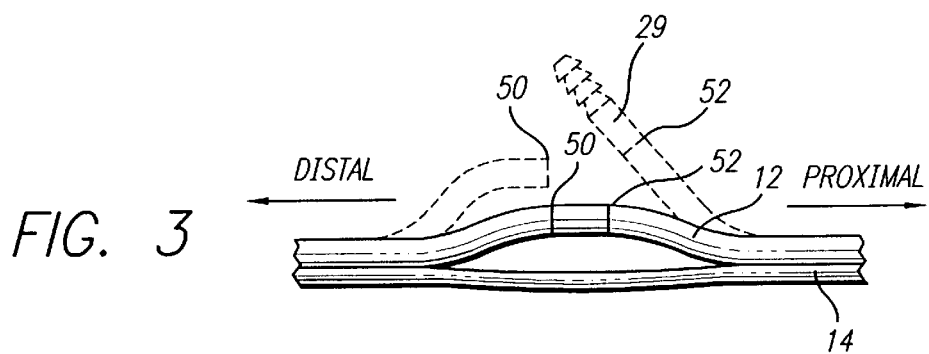
FIG. 3 is an enlarged perspective view of the severed portion of one of the tubes of the intracranial catheter of FIG. 1 showing the use of a connector to connect the two segments of the tube together.
Figure 4:
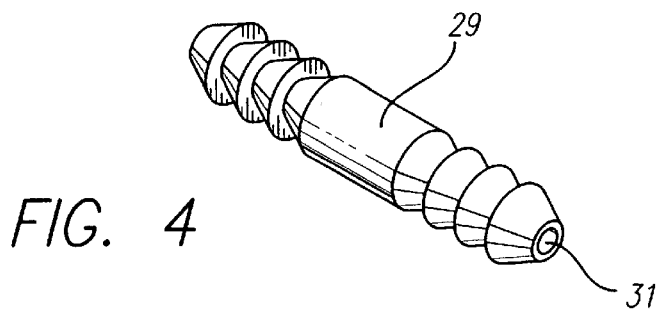
FIG. 4 is a view of a connector usable with the catheter of FIGS. 1 and 3.
Figure 5:
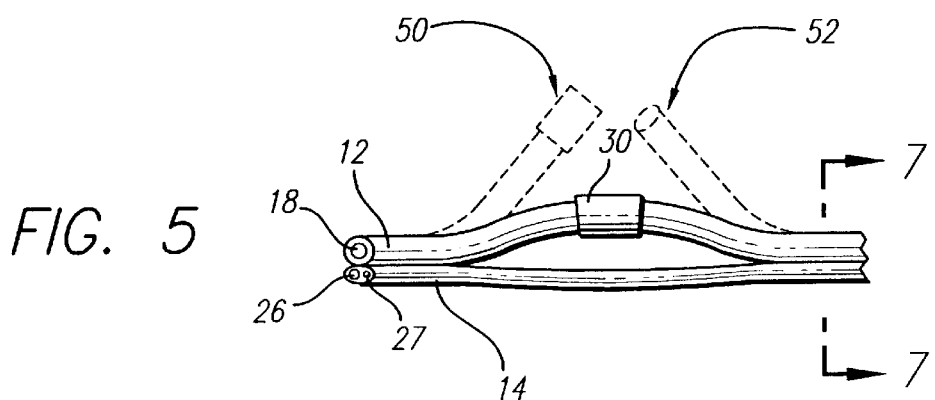
FIG. 5 shows the use of a sleeve to connect the two segments of one tube of the catheter of FIG. 1 together.

Referring now to FIGS. 3 and 5 in more detail, the drainage tube 12 has been transected or severed at a location which is preferably 200–250 mm proximal to the distal end of the catheter 10. In the specific embodiment shown, the drainage tube 12 is fully severed at such location, thereby forming first and second segments and severed ends 50, 52. A connector 29 having a lumen 31 is located between the two severed ends 50 and 52 and will be inserted into the lumina of both ends to connect them, form a fluid seal, and create a fluid channel with them such that the lumen 18 of the drainage tube 12 is thereby rendered continuous and capable of carrying fluid from the apertures 20 located at the catheter body distal end, to the proximal end of the catheter 10. The connector 29 may be disconnected from the first severed end 50 to permit a rigid stylet member 32 (FIG. 2) to be inserted into the lumen 18 of the drainage tube 12.

The preferred rigid stylet 32 comprises a blunt-tipped wire having a length which is shorter than the length of the catheter 10, but which is long enough to be inserted into the transected end of the drainage tube 12 and advanced in the distal direction through or near the distal end of the unitary distal segment DS, thereby imparting rigidity to, or rigidifying, the distal segment DS of the device.

In the preferred embodiment, the connector 29 is fixed in the lumen of the proximal segment of the drainage tube 12 by adhesive, for example, and may be disconnected from the distal segment for insertion of the stylet tube. Fixing the connector in one tubing segment assists in controlling the location of the connector and it is unlikely to be misplaced. However, in an alternate embodiment the connector 29 need not be fixed in either tube and may be disconnected from both if desired.

In one embodiment, the connector used was a double-threaded nylon straight connector made by Baxter Healthcare Corporation having part number NL850-1919. Another usable fitting or connector is a miniature barbed or threaded plastic or metal connector made by Ark-Plas Products, Inc., Highway 178N, Flippin, Ak., 72634.

In another embodiment shown in FIG. 5, a sleeve 30 is used to connect the two severed ends 50 and 52. The sleeve can be slid over both ends thereby holding them in fluid communication with each other and creating a fluid seal. The solid lines show such a configuration while the dashed lines show the segments of the drainage tube 12 separated for installation of the stylet.

As shown in FIG. 8, it is preferable that the lumen 18 of the drainage tube 12 be substantially centered within the unitary distal segment DS of the catheter such that, when the stylet 32 is inserted thereinto, the stylet will be substantially coaxially centered within the unitary distal segment DS. This facilitates a substantially uniform drainage hole pattern around the circumference of the distal segment DS.

The preferred method of using the catheter shown in FIGS. 1 through 8 is illustrated in FIGS. 9 through 13.

Initially, the connector 29 is connected to both severed ends 50, 52 of the drainage tube 12, thereby holding the transecting ends 50, 52 of the drainage tube 12 in end-to-end relation and maintaining continuity of the lumen 18 thereof. A subcutaneous tunnel ST is formed in the scalp of the patient between a first opening FO at one end thereof and a second opening SO at the opposite end thereof. A skull burr hole BH is formed beneath the second opening SO, to permit insertion of the catheter 10 into the brain.

Figure 9:
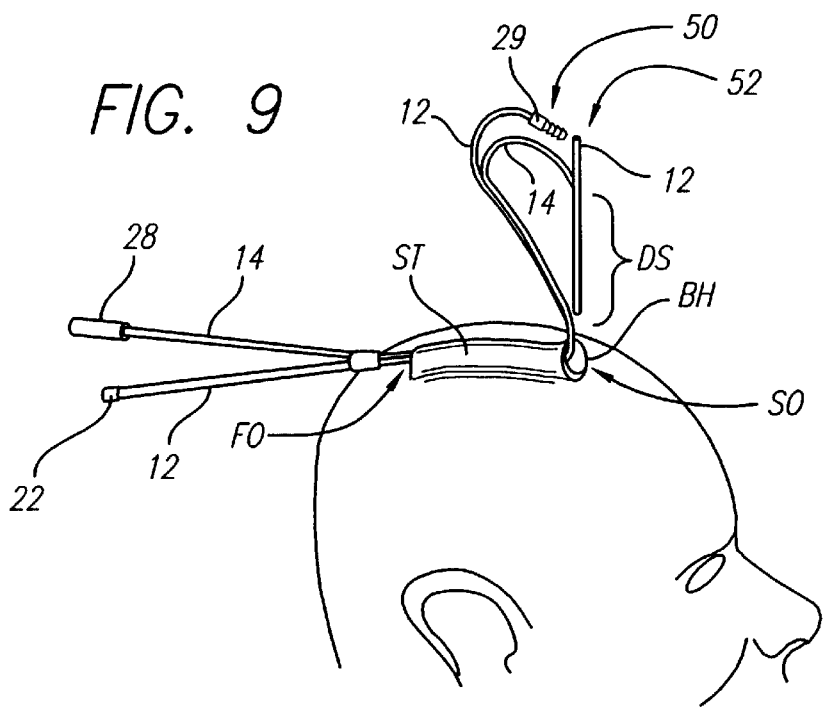
FIGS. 9 through 13 are a step-by-step showing of a preferred method of inserting the catheter of FIG. 1 through a subcutaneous tunnel formed in the scalp adjacent a skull burr hole.

The distal end of the catheter 10 is initially inserted into the first opening FO, advanced through the scalp tunnel ST, and exteriorized out of the second opening SO. A sufficient quantity of the catheter 10 is exteriorized out of the second opening SO to permit exposure and manipulation of the connector 29, as shown in FIG. 9. The connector 29 is then disconnected, separating the severed ends of the drainage tube 12.

Figure 10:
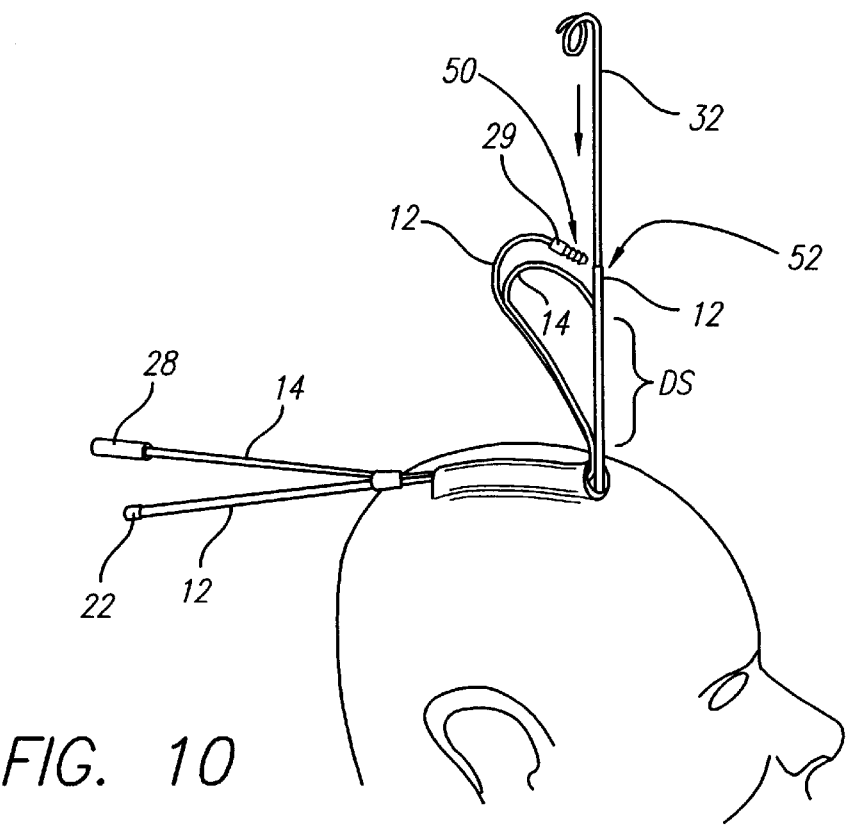

Thereafter, as shown in FIG. 10, the stylet 32 is inserted into the lumen 18 of the drainage tube 12 at the point of severance, and is advanced in the distal direction to a point where the distal end of the stylet abuts the closed distal end of the lumen 18, and extends substantially through the unitary distal segment DS of the device. With the stylet so inserted, the distal end of the device is passed through the burr hole BH and advanced downwardly into the ventricle of the brain.

Figure 11:
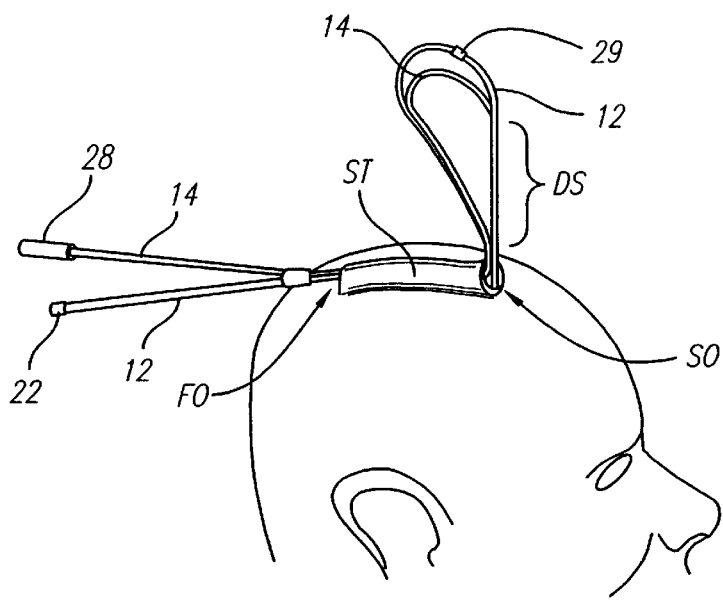

As shown in FIG. 11, after the catheter 10 has been inserted into its desired position within the brain, the stylet 32 is removed and the connector 29 is utilized to reconnect the severed ends 50, 52 of the drainage tube 12, thereby restoring the continuity and patency of the drainage catheter lumen 18.

Figure 12:
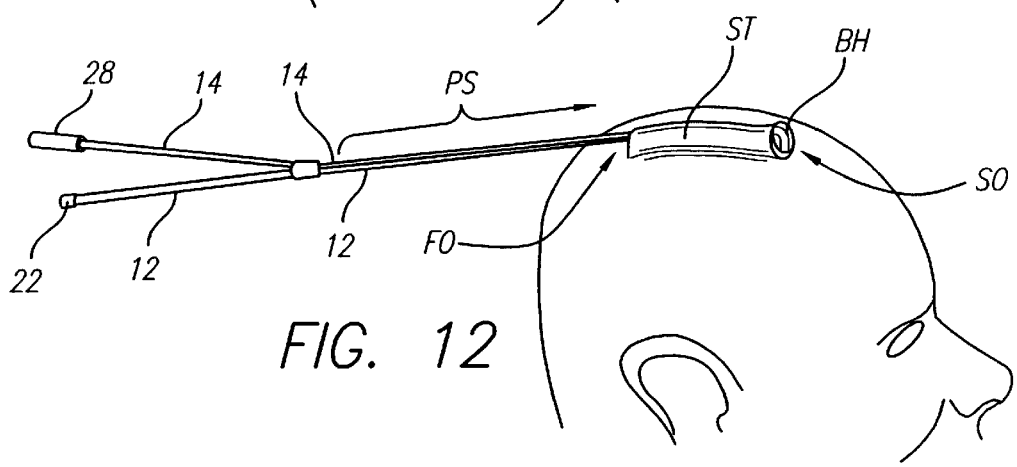

Thereafter, as shown in FIG. 12, the exteriorized slackened portion of the catheter 10 is pulled taught and the second opening SO is sutured closed.

Figure 13:
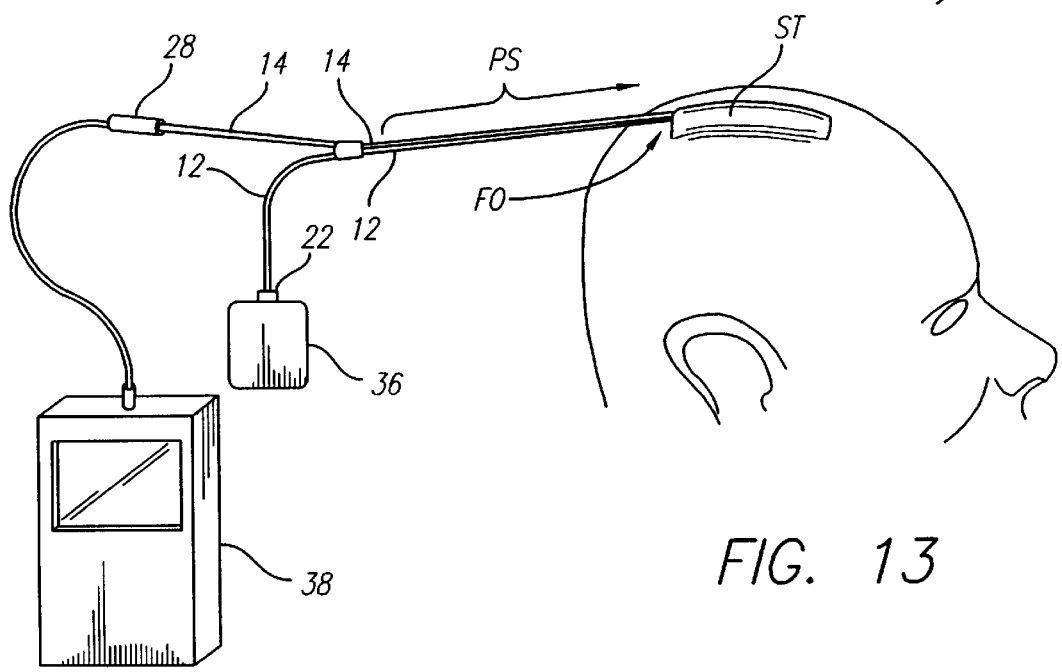

Thereafter, as shown in FIG. 13, a fluid drainage apparatus 36, such as a flexible bag to receive excess cerebrospinal fluid, is connected to the Luer connector 22 on the proximal end of the drainage tube 12 position. Also, a pressure monitoring apparatus 38 is connected to the connector 28 on the proximal end of the pressure monitoring tube 14, to provide a discernable pressure information.

In this manner, the catheter 10 is inserted through a subcutaneous scalp tunnel ST and the second opening SO is fully sutured closed after the catheter 10 has been inserted, thereby minimizing the likelihood that pathogens will pass through the skull burr hole BH during the period of time that the catheter 10 remains indwelling. The monitor 38 will provide a continual monitoring of the intracranial pressure, at the distal end of the unitary distal segment DS of the device. When it is determined that the intracranial pressure has risen to an undesirable level, the cerebrospinal fluid may be vented or removed from the intracranial space by use of the fluid drainage apparatus 36.

The present invention has been described hereabove with the reference to certain presently preferred embodiments of the device and its method of use. It will be appreciated that various additions, deletions, alterations and modifications may be made to the above-described embodiments without departing from the intended spirit and scope of the invention. Accordingly, it is intended that all such reasonable additions, deletions, alterations and modifications be included within the scope of the invention unless limited by the appended claims.

What is claimed is:

1. A catheter, comprising:
    first and second elongate tubes, each tube having a respective outer surface and a lumen and each tube having distal and proximal ends;
    wherein the first and second tubes are joined together at their distal ends to form a single tube defining a catheter body distal end with a single outer surface, with the lumina of the first and second tubes remaining separate in the catheter body distal end;
    the first tube having first and second segments with the first segment being located distally to the second segment, the lumen of the first segment terminating in a closed end in the catheter body distal end, and the first and second segments being severed from each other at a severance location proximal to the catheter body distal end; and
    a connector engaged with the first and second segments and connecting the first and second segments together at the severance location, the connector forming a fluid-tight seal with the first and second segments and the connector being disconnectable from a segment;
    wherein the length of the lumen of the first segment continuing into the catheter body distal end and the diameter of the lumen are selected to receive a stylet so that the stylet can be introduced through the first segment lumen at the severance location when the connector is disconnected and extended to the closed end of the segment.

2. The catheter of claim 1 further comprising drainage apertures formed at the catheter body distal end in fluid communication with one of the lumina of the first and second tubes.

3. The catheter of claim 2 further comprising:
    a sensor located in one of the lumina of the first and second tubes, the sensor located so as to sense a selected parameter at the distal end of the catheter body; and
    energy conducting devices connected to the sensor, the energy conducting devices disposed in one of the lumina of the first and second tubes and extending to the proximal end of the catheter body.

4. The catheter of claim 3 wherein the sensor comprises a pressure sensor disposed in the lumen of the second tube in the catheter body distal end; and
    the energy conducting devices comprise optical fibers extending from the pressure sensor to the proximal end of the lumen.

5. The catheter of claim 1 further comprising a sensor located in one of the lumina of the first and second tubes, the sensor located so as to sense a selected parameter at the distal end of the catheter body.

6. The catheter of claim 5 further comprising energy conducting devices connected to the sensor, the energy conducting devices disposed in one of the lumina of the first and second tubes and extending to the proximal end of the catheter body.

7. The catheter of claim 6 wherein the energy conducting devices comprise optical fibers coupled to the sensor and extending to the proximal end of the lumen in which they are disposed.

8. The catheter of 5 wherein:
    the sensor comprises a pressure sensor disposed in the catheter body distal end; and
    the energy conducting devices comprise optical fibers extending from the pressure sensor to the proximal end of the lumen.

9. The catheter of claim 6 wherein the sensor and energy conducting devices are located in the catheter body distal end in the lumen of the second tube extending into the catheter body distal end.

10. The catheter of claim 1 wherein the connector comprises an internal connector disposed in the lumina of both the first and second segments, the connector having a fluid lumen that is in fluid communication and interconnects the lumina of the first and second segments.

11. The catheter of claim 10 wherein the connector is fixed in position in the distal end of the second segment but may be disconnected from the proximal end of the first segment so that a stylet may be inserted into the proximal end of the first segment.

12. The catheter of claim 1 wherein the connector comprises a slidable sleeve disposed on one of the first and second segments and slidable over the other segment for forming a fluid-tight seal between the first and second segments.

13. A catheter, comprising:

first and second elongated tubes, each tube having a respective outer surface and a lumen and each tube having distal and proximal ends;

wherein the first and second tubes are joined together at their distal ends to form a single tube defining a catheter body distal end having a single outer surface, with the lumina of the first and second tubes remaining separate in the catheter body distal end;

the first tube having first and second segments with the first segment being located distally to the second segment, the lumen of the first segment terminating in a closed end in the catheter body distal end, and the first and second segments being severed from each other at a severance location proximal to the catheter body distal end;

a connector engaged with the first and second segments and connecting the first and second segments together at the severance location, the connector forming a fluid-tight seal with the first and second segments and the connector being disconnectable from a segment; and drainage apertures formed at the catheter body distal end in fluid communication with the lumen of the first tube;

wherein the length of the lumen of the first segment continuing into the catheter body distal end and the diameter of the lumen are selected to receive a stylet so that the stylet can be introduced through the first segment lumen at the severance location when the connector is disconnected and extended to the closed end of the segment.

14. The catheter of claim 13 further comprising a sensor located in one of the lumina of the first and second tubes, the sensor located so as to sense a selected parameter at the distal end of the catheter body.

15. The catheter of claim 14 further comprising energy conducting devices connected to the sensor, the energy conducting devices disposed in one of the lumina of the first and second tubes and extending to the proximal end of the catheter body.

16. The catheter of claim 15 wherein the sensor and energy conducting devices are located in the catheter body distal end in the lumen of the second tube extending into the catheter body distal end.

17. The catheter of 14 wherein:

the sensor comprises a pressure sensor disposed in the catheter body distal end; and the energy conducting devices comprise optical fibers extending from the pressure sensor to the proximal end of the lumen.

18. The catheter of claim 13 wherein the connector comprises an internal connector disposed in the lumina of both the first and second segments, the connector having a fluid lumen that is in fluid communication and interconnects the lumina of the first and second segments.

19. The catheter of claim 18 wherein the connector is fixed in position in the distal end of the second segment but may be disconnected from the proximal end of the first segment so that a stylet may be inserted into the proximal end of the first segment.

20. The catheter of claim 13 wherein the connector comprises a slidable sleeve disposed on one of the first and second segments and slidable over the other segment for forming a fluid-tight seal between the first and second segments.

21. An intracranial catheter comprising:

a drainage catheter portion having a proximal end, a distal end, at least one drainage aperture at the distal end and a lumen extending therethrough from said at least one drainage aperture to the proximal end of said drainage catheter portion;

a sensor catheter portion having a proximal end, a distal end and a sensor at the distal end operative to sense a physical parameter and to transmit sensor signals to the proximal end of said sensor catheter portion;

said drainage catheter portion and said sensor catheter portion being disposed in side-by-side relation to one another, with distal segments of said drainage catheter portion and said sensor catheter portion being fused to comprise a unitary distal segment of said catheter;

a stylet insertion opening formed in said drainage catheter portion at a stylet insertion location which is proximal to the unitary distal segment of said catheter but distal to the proximal end of said drainage catheter portion, said opening extending into said lumen such that a rigid stylet may be inserted through said opening and advanced into said lumen;

a closure apparatus for closing said stylet insertion aperture when no stylet is inserted therethrough, said closure apparatus being operative to seal said lumen such that fluid may pass through said lumen from said at least one drainage aperture to the proximal end of said drainage catheter portion; and a transecting cut through said drainage catheter portion at said stylet insertion location so as to form first and second severed ends of said drainage catheter portion;

wherein said closure apparatus comprises a disconnectable internal connector operative to join the severed ends of said drainage catheter in end-to-end fashion.

22. The catheter of claim 21 wherein said sensor comprises:

a pressure sensor located at a pressure sensing location on the unitary distal segment of said catheter; and a fiber optic pathway extending longitudinally through said sensor catheter portion to transmit optical indicia of pressure from said pressure sensor to the proximal end of said sensor catheter portion.

23. The catheter of claim 22 wherein the unitary distal segment of said catheter has a distal end, and wherein said pressure sensing location is on the distal end of said unitary distal segment of said device.

24. The catheter of claim 21 wherein said internal connector is permanently connected to one severed end of said drainage catheter, and releasably connectable to the other severed end of said drainage catheter, such that the severed ends of said drainage catheter may be temporarily separated to permit said stylet to be inserted into the unitary distal segment of said catheter, and further such that said severed ends may be subsequently reconnected by said internal connector after said stylet has been removed.

25. The catheter of claim 21 further in combination with an elongate stylet member insertable through said stylet insertion opening to rigidify the unitary distal segment of said catheter.

26. The catheter of claim 21 wherein said unitary distal segment of said catheter has a generally cylindrical side wall, and wherein said at least one drainage aperture comprises a plurality of drainage apertures formed in the side wall of said drainage catheter, near the distal end thereof, in communication with said lumen.

27. The catheter of claim 21 further comprising an elongate tensile member having two ends and extending longitudinally through said sensor catheter portion and anchored at both said tensile member ends to control stretching of the sensor catheter portion.

* * * * *